United States Patent [19]

Chang et al.

[11] Patent Number: 6,166,240
[45] Date of Patent: Dec. 26, 2000

[54] PROCESS FOR CO-PRODUCTION OF DIALKYL CARBONATE AND ALKANEDIOL

[75] Inventors: Clarence D. Chang, Princeton; Larry E. Hoglen, Mickelton; Zhaozhong Jiang, Thorofare; Rene B. LaPierre, Medford, all of N.J.

[73] Assignee: Mobil Oil Corporation, Fairfax, Va.

[21] Appl. No.: 09/507,843

[22] Filed: Feb. 22, 2000

[51] Int. Cl.[7] .................................................. C07C 68/06
[52] U.S. Cl. .............................................................. 558/277
[58] Field of Search ............................................. 558/277

[56] References Cited

U.S. PATENT DOCUMENTS

| | | |
|---|---|---|
| 3,642,858 | 2/1972 | Frevel et al. . |
| 4,062,884 | 12/1977 | Romano et al. . |
| 4,181,676 | 1/1980 | Buysch . |
| 4,391,739 | 7/1983 | Chu . |
| 4,434,105 | 2/1984 | Buysch et al. . |
| 4,661,609 | 4/1987 | Knifton . |
| 4,686,274 | 8/1987 | Harris et al. . |
| 4,691,041 | 9/1987 | Duranleau et al. . |
| 4,895,970 | 1/1990 | Harris . |
| 5,015,753 | 5/1991 | Harris . |
| 5,196,561 | 3/1993 | Mori et al. ............................... 558/277 |
| 5,218,135 | 6/1993 | Buysch et al. . |
| 5,231,212 | 7/1993 | Buysch et al. . |
| 5,292,980 | 3/1994 | Dessau . |
| 5,387,708 | 2/1995 | Molzahn et al. . |
| 5,391,803 | 2/1995 | King et al. . |
| 5,403,949 | 4/1995 | Manada et al. .......................... 558/277 |
| 5,430,170 | 7/1995 | Urano et al. . |
| 5,436,362 | 7/1995 | Kondoh et al. . |
| 5,489,703 | 2/1996 | Pacheco et al. . |
| 5,498,743 | 3/1996 | Shih et al. . |
| 5,663,480 | 9/1997 | Tsuneki et al. . |
| 5,847,189 | 12/1998 | Tojo et al. . |

FOREIGN PATENT DOCUMENTS

| | | |
|---|---|---|
| 0 478 073 A2 | 9/1991 | European Pat. Off. . |
| 3-44354 | 2/1991 | Japan . |
| 6-107601 | 4/1994 | Japan . |

OTHER PUBLICATIONS

Chang, C.D., *Handbook of Heterogenous Catalysis*, Wiley–VCH:Weinheim, Germany, vol. 4, Chapter 3.7 (1997).

Yagi, F., Kanuka, N., Tsuji, H., Nakata, S., Kita, H. and Hattori, H., "$^{133}$Cs and $^{23}$Na MAS NMR studies of zeolite X containing cesium," *Microporous Materials* 9:229–235(1997).

Skibsted, J., Vosegaard, T., Bildsøe, H. and Jakobsen, H.J., "$^{133}$Cs chemical Shielding Anisotropics and Quadrupole Couplings from Magic–Angle Spinning NMR of Cesium Salts," *J. Phys. Chem.*, 100:14872–14881(1996).

Knifton, J.F. and Duranleau, R.G., "Ethylene Glycol–Dimethyl Carbonate Cogeneration," *J. of Molecular Catalysis* 67:389–399(1991).

Watanabe, Y. and Tatsumi T., "Hydrotalcite–type Materials as Catalysts for the Synthesis of Dimethyl Carbonate from Ethylene Carbonate and Methanol[1]," *Microporous and Mesoporous Materials* 22:399–407(1998).

*Primary Examiner*—Michael G. Ambrose
*Attorney, Agent, or Firm*—Malcolm D. Keen

[57] ABSTRACT

A method is provided for co-producing dialkyl carbonate and alkanediol by reacting alkylene carbonate with alkanol in the presence of a Group 5 or Group 6 metal oxide catalyst.

10 Claims, No Drawings

PROCESS FOR CO-PRODUCTION OF DIALKYL CARBONATE AND ALKANEDIOL

BACKGROUND

This invention relates to a method of co-producing dialkyl carbonate and alkanediol and, in particular, to a method of co-producing dialkyl carbonate and alkanediol through the use of a Group 5 or Group 6 metal oxide catalyst.

Various homogeneous catalysts have been proposed for carbonate transesterification. For example, U.S. Pat. Nos. 3,642,858 and 4,181,676 disclose the preparation of dialkyl carbonates by transesterifying alkylene carbonates with alcohols in the presence of alkali metals or alkali metal compounds without the use of a support material. U.S. Pat. No. 4,661,609 teaches the use of a catalyst selected from the group consisting of zirconium, titanium and tin oxides, salts or complexes thereof.

Commercial use of homogeneous catalysts is restricted because separation of the catalyst from the unconverted reactants and organic product can be difficult. Because the transesterification is an equilibrium reaction, in an attempt to isolate the intended dialkyl carbonate by distillation of the reaction liquid without advance separation of the catalyst, the equilibrium is broken during the distillation and a reverse reaction is induced. Thus, the dialkyl carbonate once formed reverts to alkylene carbonate. Furthermore, due to the presence of the homogenous catalyst, side reactions such as decomposition, polymerization, or the like concurrently take place during the distillation which decrease the efficiency.

Various heterogenous catalysts have also been proposed for carbonate transesterification. The use of alkaline earth metal halides is disclosed in U.S. Pat. No. 5,498,743. Knifton, et al., "Ethylene Glycol-Dimethyl Carbonate Cogeneration," *J. Molec. Catal* 67:389–399 (1991) disclose the use of free organic phosphines or organic phosphines supported on partially cross-linked polystyrene. U.S. Pat. No. 4,691,041 discloses the use of organic ion exchange resins, alkali and alkaline earth silicates impregnated into silica, and certain ammonium exchanged zeolites. U.S. Pat. No. 5,430,170 discloses the use of a catalyst containing a rare earth metal oxide as the catalytically active component. The use of $MgO/Al_2O_3$ hydrotalcites is disclosed in Japanese patent application 3[1991]-44,354. The use of MgO is disclosed in Japanese Unexamined Patent Application 6[1994]-107,601. The use of zeolites ion-exchanged with alkali metal and/or alkaline earth metal, thereby containing a stoichiometric amount of metal, are disclosed in U.S. Pat. No. 5,436,362.

European Patent Application 0 478 073 A2 discloses a process for producing a dialkyl carbonate by contacting an alkylene carbonate with an alkanol in the presence of a mixed metal oxide, i.e., a catalyst containing two or more metal oxides. Unlike the process disclosed in the European application, the method of the invention does not utilize a mixed metal oxide catalyst. Rather, the method of the invention utilizes a catalyst which is a single Group 5 or Group 6 metal oxide compound.

Inorganic heterogenous catalysts generally possess thermal stability and easy regeneration. However, these catalysts, including the zeolites containing a stoichiometric amount of alkali or alkaline earth metal, generally demonstrate low activity and/or selectivity and are unsatisfactory for commercial application.

Polymer supported organic phosphines and ion exchange resins show high activity and good to excellent selectivity in transesterification reaction between alkylene carbonate and alkanol; however, these polymeric materials do not appear very stable and gradually lose catalytic activity, especially at relatively high temperatures.

Thus, there remains a need for a method of transesterifying alkylene carbonate with alkanol to co-produce dialkyl carbonate and alkanediol that will provide higher feed conversion and product selectivity over a wide temperature range.

SUMMARY OF INVENTION

A method is provided for co-producing dialkyl carbonate and alkanediol by reacting alkylene carbonate with alkanol in the presence of a Group 5 or Group 6 metal oxide catalyst. Ethylene carbonate and methanol are preferred reagents.

In a preferred embodiment, the Group 6 metal oxide catalyst has a formula $AO_3$, wherein A is a Group 6 metal and O is oxygen. Preferred Group 6 metals are molybdenum and tungsten. For example, $MoO_3$ is a preferred catalyst. In a separate preferred embodiment, the catalyst has a formula $X_2O_5$, wherein X is a Group 5 metal and O is oxygen.

In a separate preferred embodiment, the catalyst is supported on a porous inorganic substrate, for example, silica, alumina, zirconia, mesoporous materials, or a combination thereof. Silica is preferred.

The process conditions of the method of the invention include a reaction temperature of about 20° C. (68° F.) to about 300° C. (572° F.), a reaction pressure of about 14 to about 4000 psig, a liquid hourly space velocity of about 0.1 to 40 $hr^{-1}$, and a molar ratio of alkanol to alkylene carbonate of about 1–20.

Unlike polymer catalysts such as ion exchange resins, the Group 5 or Group 6 metal oxide catalysts used in the method of the invention are thermally stable and regenerable. The combination of good catalytic activity and high selectivity in a wide temperature range, and thermal stability and regenerability of the catalysts, render them suitable for commercial use in co-producing organic carbonate and alkanediol through ester exchange reaction. Also, the general availability and low cost of the catalysts could significantly improve the process economics.

The organic carbonates produced by the method of the invention, dimethyl carbonate in particular, have potential application as "green" replacements for phosgene that is used mainly in manufacture of polyurethane and polycarbonate resins. Dimethyl carbonate can also be used as a fuel additive and methylating agent in fine chemical synthesis.

DETAILED DESCRIPTION OF INVENTION

In accordance with the present invention, a method is provided for the co-production of dialkyl carbonate and alkanediol through the transesterification of alkylene carbonate with alkanol using a Group 5 or Group 6 metal oxide catalyst.

Generally, all alkylene carbonates can be used as a reactant in this invention. However, lower alkylene carbonate such as ethylene carbonate, propylene carbonate, butylene carbonate or the like is preferred; ethylene carbonate or propylene carbonate is most preferred.

Generally, all alkanol reactants can be used, provided the alkanol reacts with cyclocarbonate to produce the dialkyl carbonate and alkanediol product. However, an aliphatic or aromatic alkanol having 1 to 10 carbon atoms is preferably used. For example, methanol, ethanol, n-propanol, iso-propanol, n-butanol, iso-butanol, secondary butanol, tertiary butanol, allyl alcohol, pentanol, cyclo-hexanol, benzyl alcohol, 2-phenyl ethyl alcohol, 3-phenyl propyl alcohol, 2-methoxy ethanol or the like can be used as the aliphatic or aromatic alcohol. A lower aliphatic alcohol such as methanol or ethanol is most preferably used due to its reactivity and low cost.

Further, a phenolic compound can be used in place of the alcoholic compound as the compound which has a hydroxyl (OH) group and reacts with cyclocarbonate to produce the carbonate.

The catalyst of the invention can have either the formula $AO_3$ wherein A is a Group 6 metal and O is oxygen, or $X_2O_5$ wherein X is a Group 5 metal and O is oxygen. The Group 6 metals are those listed as Group 6 (CAS version VIB) of the Periodic Table of Elements. Preferred Group 6 metals include molybdenum and tungsten. Chromium is not preferred. The Group 5 metals (CAS version VB) are those listed as Group 5 in the Periodic Table of Elements.

A high surface area is preferred in the method of the invention. The catalysts used in the method of the invention typically have a surface area of between about 5–600 $m^2/g$. A surface area above 50 $m^2/g$ is preferred.

The catalyst can be supported on a conventional porous, inorganic substrate. Preferred porous inorganic substrates include silica, alumina, zirconia, mesoporous materials, such as MCM-41 and MCM-48, or a combination of these substrates. Silica is most preferred.

The weight ratio of the catalyst to substrate can be a wide range and is generally in the range from about 10:90 to about 90:10. The catalyst and the substrate can be combined by any means known to one skilled in the art such as stirring, blending, kneading, or extrusion, followed by drying. The catalyst-substrate combination can be dried in air or an inert gas at a temperature usually in the range of from about 10° C. to about 150° C. for about 0.5 to about 12 hours. The dried catalyst-binder combination can also be further calcined, if desired, in the presence of air or an inert gas at a temperature usually from about 400° C. to 700° C., preferably about 450° C. to about 600° C., for about 1 to about 12 hours. If a binder is not used, the catalyst can also be calcined alone under similar conditions to remove any contaminants, if present.

In a preferred method for supporting the catalyst on the substrate, the substrate is mixed with an aqueous solution of a catalyst precursor followed by evaporating/removing excess amount of water, drying the resultant supported catalyst at mild temperatures (50–150° C.), and calcining at high temperatures (>400° C.). The precursor material necessarily contains the Group 5 or Group 6 metal of the catalyst. The final calcination step converts the soluble catalyst precursor to an active catalyst.

The reactor type in this invention can be any type generally known, such as a continuous fluid bed, fixed bed or stirred tank, etc. Since the catalyst used in the method of the invention is heterogeneous, it is preferred that a fixed bed be used so as to avoid the expense of having to recover the catalyst from the reagents.

The reaction conditions can vary and should be optimized in order to yield a relatively high conversion and selectivity for the desired products. Although a batch operation is contemplated, the reaction will preferably be carried out in a continuous mode utilizing various reactor configurations.

Typical reaction conditions of this invention include a reaction temperature of about 20° C. to about 300° C., preferably about 60° C. to about 175° C.; a reaction pressure of about 14 to about 4000 psig, preferably about 50 to about 400 psig; a liquid hourly space velocity of about 0.1 to about 40 $hr^{-1}$, preferably about 0.5 to about 10 $hr^{-1}$; and a molar ratio of alkanol to alkylene carbonate of about 1 to 20, preferably about 2 to 8.

The products from the reaction of this invention are recovered and can be separated by distillation, azeotropic distillation, extraction or other techniques well known in the art.

The following examples are provided to assist in a further understanding of the invention. The particular materials and conditions employed are intended to be further illustrative of the invention and are not limiting upon the reasonable scope thereof.

EXAMPLE 1

This example describes a method for preparing a catalyst employed in the method of the invention, i.e. silica supported molybdenum trioxide ($MoO_3/SiO_2$). Ammonium molybdate tetrahydrate (33.2g) was dissolved in 500 cc de-ionized water, and the resultant solution was stirred and mixed with 200 g of silica gel (Davisil, grade 643, 200–425 mesh) for 2 h. At the end of this period, the mixture was evaporated to dryness at 60° C. using a rotary evaporator. The remaining solid catalyst was dried in an oven at 120° C. overnight and then calcined in air at 550° C. Ammonium molybdate was decomposed quantitatively to $MoO_3$ during the calcination process. The calcined catalyst had a BET surface area of 93 $m^2/g$, and contained 10.2 wt % molybdenum and 2 ppm nitrogen.

EXAMPLE 2

A transesterification evaluation was performed for the catalyst described in Example 1.

The transesterification reaction was performed in a fixed bed micro-unit equipped with a three-zone furnace and a down-flow trickle-bed tubular reactor (½" ID). Catalyst powder was pelletized and sized to 60–80 mesh. The reactor was loaded with a mixture of 10 cc of the sized catalyst and 3 cc of 80–120 mesh sand.

After pressure testing of the unit, the catalyst was dried at 400° F. for two hours under 1 atmosphere, 170 cc/min nitrogen flow. At the end of this period, the reactor was cooled down to 150° F. and nitrogen flow was stopped. The reactor pressure, controlled by a pressure regulator, was then set to 100 psig, and the ethylene carbonate (EC)/methanol (MeOH) mixture feed was pumped and added to the top of the reactor at 1.0 $h^{-1}$ LHSV. After the reactor was conditioned for 8 h, the reactor temperature was increased to initial operating temperature. Liquid products were condensed in a stainless steel dropout pot at −10° C. Both liquid and off-gas products were analyzed by GC. The catalytic reaction was studied at various temperatures and LHSV to vary EC conversion.

The catalyst was evaluated according to the procedures described above. Detailed operating conditions and results on EC conversion and dimethyl carbonate (DMC)/ethylene glycol (EG) selectivities for the $MoO_3/SiO_2$ catalyst are summarized in Table 1.

Feed conversion is calculated based on EC converted during the transesterification reaction, since excess amount of MeOH relative to EC was used for all reactions. During EC/MeOH reaction, 2-hydroxyethyl methyl carbonate (HEMC) intermediate was also formed in addition to DMC and EG. The concentration of HEMC varies depending on the reaction conditions.

Since it is recyclable along with unreacted EC, the intermediate carbonate is not considered as a byproduct. The feed conversion and product selectivity are defined as follows:

EC Conversion=(EC converted to products other than HEMC)/(total EC in feed);

DMC Selectivity=(moles of DMC formed)/(moles of EC converted to products other than HEMC);

EG Selectivity=(moles of EG formed)/(moles of EC converted to products other than HEMC).

TABLE 1

MoO$_3$/SiO$_2$-Catalyzed Transesterifiction of Ethylene Carbonate with Methanol (Condition: 100 psig)

| Temperature, °F./°C. | 275/135 | 300/149 | 325/163 | 300/149 |
|---|---|---|---|---|
| LHSV, h$^{-1}$ | 1.0 | 1.0 | 1.0 | 0.5 |
| Feed Composition | | | | |
| MeOH/EC, molar ratio | 3.9 | 3.9 | 3.9 | 3.9 |
| Total Liquid Product Composition | | | | |
| MeOH, wt % | 51.7 | 48.8 | 45.9 | 45.2 |
| EC, wt % | 29.0 | 19.1 | 17.9 | 15.5 |
| HEMC Intermediate, wt % [a] | 10.2 | 12.8 | 7.9 | 10.3 |
| DMC, wt % | 5.1 | 11.0 | 16.4 | 16.8 |
| EG, wt % | 4.1 | 8.2 | 11.8 | 12.2 |
| DMC/EG, Molar Ratio | 0.86 | 0.93 | 0.96 | 0.95 |
| EC Conv., % | 13.8 | 290 | 41.5 | 43.0 |
| DMC Select., % | 85.5 | 92.7 | 95.6 | 94.5 |
| EG Select., % | 99.7 | 100.0 | 99.6 | 99.4 |

[a] HEMC: 2-hydroxyethyl methyl carbonate - an intermediate carbonate formed during the reaction of ethylene carbonate with methanol The examples demonstrate that the transesterification catalysts of the current invention exhibit good activity and very high selectivity in the reaction of alkylene carbonate with alkanol.

More specifically, the MoO$_3$/SiO$_2$ catalyst demonstrated an EC conversion of approximately 29–43% within the operating temperatures of 300° F.–325° F. at 1.0 hr$^{-1}$ LHSV. At a given temperature, the conversion increases upon decreasing the feed LHSV (or increasing the catalyst/feed contact time). For example, the EC conversion at 300° F. changed from 29% to 43% when the feed rate was reduced from 1.0 hr$^{-1}$ LHSV to 0.5 hr$^{-1}$ LHSV. The DMC selectivity was between approximately 86–96% for the full range of tested operating temperatures, i.e. 275° F.–325° F. The EG selectivity was even greater at about 100% for the full range of operating temperatures.

Therefore, the method of the invention is adaptable to commercial application because of the good level of activity, very high selectivity over a wide temperature range, and the stability and relatively low cost of the transition metal oxide catalyst used.

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

We claim:

1. A method for co-producing dialkyl carbonate and alkanediol comprising reacting alkylene carbonate with alkanol in the presence of a Group 5 or Group 6 metal oxide catalyst.

2. The method of claim 1 wherein said Group 6 metal oxide catalyst has a formula AO$_3$, wherein A is a Group 6 metal and O is oxygen.

3. The method of claim 1 wherein said Group 5 metal oxide catalyst has a formula X$_2$O$_5$, wherein X is a Group 5 metal and O is oxygen.

4. The method of claim 2 wherein said Group 6 metal is selected from the group consisting of molybdenum or tungsten.

5. The method of claim 1 wherein said catalyst is MoO$_3$.

6. The method of claim 1 wherein said alkylene carbonate is ethylene carbonate and said alkanol is methanol.

7. The method of claim 1 wherein said catalyst is supported on a porous inorganic substrate.

8. The method of claim 7 wherein said substrate is selected from the group consisting of silica, alumina, zirconia, mesoporous materials, or a combination thereof.

9. The method of claim 8 wherein said substrate is silica.

10. The method of claim 1 wherein reaction temperature is about 20° C. to about 300° C., reaction pressure is about 14 to about 4000 psig, liquid hourly space velocity is about 0.1 to about 40 hr$^{-1}$, and molar ratio of alkanol to alkylene carbonate is about 1–20.

* * * * *